United States Patent
Hempel et al.

(10) Patent No.: US 8,655,432 B2
(45) Date of Patent: Feb. 18, 2014

(54) METHOD AND COMPUTER UNIT FOR SETTING A CONTRAST AGENT INJECTION PUMP FOR IMAGE RECORDING

(75) Inventors: Eckhard Hempel, Fürth (DE); Matthias Niethammer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1934 days.

(21) Appl. No.: 11/826,434

(22) Filed: Jul. 16, 2007

(65) Prior Publication Data

US 2008/0027309 A1 Jan. 31, 2008

(30) Foreign Application Priority Data

Jul. 17, 2006 (DE) .......................... 10 2006 032 991

(51) Int. Cl.
*A61B 6/00* (2006.01)

(52) U.S. Cl.
USPC ........... 600/431; 600/407; 600/420; 600/432; 604/131; 604/151; 604/890.1

(58) Field of Classification Search
USPC .................... 600/407, 431, 425, 432; 378/42; 604/131, 151, 890.1
See application file for complete search history.

(56) References Cited

U.S. PATENT DOCUMENTS

| 5,687,208 | A | 11/1997 | Bae et al. | |
|---|---|---|---|---|
| 6,397,098 | B1* | 5/2002 | Uber et al. | 600/431 |
| 7,974,682 | B2* | 7/2011 | Gonzalez Molezzi et al. | 600/432 |
| 8,055,045 | B2* | 11/2011 | Kokubun et al. | 382/131 |
| 8,197,437 | B2* | 6/2012 | Kalafut et al. | 604/67 |
| 2001/0054695 | A1* | 12/2001 | Lienard et al. | 250/368 |
| 2010/0030073 | A1* | 2/2010 | Kalafut | 600/431 |
| 2011/0208046 | A1* | 8/2011 | Gonzalez Molezzi et al. | 600/431 |
| 2012/0051614 | A1* | 3/2012 | Olszewski et al. | 382/128 |

FOREIGN PATENT DOCUMENTS

| DE | 197 02 896 A1 | 7/1997 |
|---|---|---|
| DE | 696 31 607 T2 | 3/2004 |

* cited by examiner

Primary Examiner — Unsu Jung
Assistant Examiner — Amanda Lauritzen Moher
(74) Attorney, Agent, or Firm — Harness, Dickey & Pierce, P.L.C.

(57) ABSTRACT

A method is proposed for simple and quick setting of an injection pump for image recording. In at least one embodiment of the method, patient-specific and appliance-specific input parameters are entered and a contrast agent protocol is created from the patient-specific and appliance-specific input parameters, by computer, by way of a functional relationship, and the contrast agent protocol is output to the injection pump. Furthermore, a computer unit is provided in at least one embodiment, with the aid of which the method is carried out.

14 Claims, 2 Drawing Sheets

FIG 2

| Volume Phase 1 [ml] | | | | | | | | | | | |
|---|---|---|---|---|---|---|---|---|---|---|---|
| Patient weight [kg]: | 0-5 | 5-10 | 10-15 | 15-25 | 25-35 | 35-45 | 45-55 | 55-65 | 65-85 | 85-95 | 95-max |
| Scan duration [s] | | | | | | | | | | | |
| 0 | 8.6 | 17.1 | 25.7 | 42.9 | 60.0 | 77.1 | 94.3 | 111.4 | 145.7 | 162.9 | 180.0 |
| 2 | 8.6 | 17.1 | 25.7 | 42.9 | 60.0 | 77.1 | 94.3 | 111.4 | 145.7 | 162.9 | 180.0 |
| 4 | 8.6 | 17.1 | 25.7 | 42.9 | 60.0 | 77.1 | 94.3 | 111.4 | 145.7 | 162.9 | 180.0 |
| 6 | 8.6 | 17.1 | 25.7 | 42.9 | 60.0 | 77.1 | 94.3 | 111.4 | 145.7 | 162.9 | 180.0 |
| 8 | 8.6 | 17.1 | 25.7 | 42.9 | 60.0 | 77.1 | 94.3 | 111.4 | 145.7 | 162.9 | 180.0 |
| 10 | 8.6 | 17.1 | 25.7 | 42.9 | 60.0 | 77.1 | 94.3 | 111.4 | 145.7 | 162.9 | 180.0 |
| 12 | 8.6 | 17.1 | 25.7 | 42.9 | 60.0 | 77.1 | 94.3 | 111.4 | 145.7 | 162.9 | 180.0 |
| 14 | 8.6 | 17.1 | 25.7 | 42.9 | 60.0 | 77.1 | 94.3 | 111.4 | 145.7 | 162.9 | 180.0 |
| 16 | 8.6 | 17.1 | 25.7 | 42.9 | 60.0 | 77.1 | 94.3 | 111.4 | 145.7 | 162.9 | 180.0 |
| 18 | 8.6 | 17.1 | 25.7 | 42.9 | 60.0 | 77.1 | 94.3 | 111.4 | 145.7 | 162.9 | 180.0 |
| 20 | 8.6 | 17.1 | 25.7 | 42.9 | 60.0 | 77.1 | 94.3 | 111.4 | 145.7 | 162.9 | 180.0 |
| 22 | 8.6 | 17.1 | 25.7 | 42.9 | 60.0 | 77.1 | 94.3 | 111.4 | 145.7 | 162.9 | 180.0 |
| 24 | 8.6 | 17.1 | 25.7 | 42.9 | 60.0 | 77.1 | 94.3 | 111.4 | 145.7 | 162.9 | 180.0 |
| 26 | 8.6 | 17.1 | 25.7 | 42.9 | 60.0 | 77.1 | 94.3 | 111.4 | 145.7 | 162.9 | 180.0 |
| 28 | 8.6 | 17.1 | 25.7 | 42.9 | 60.0 | 77.1 | 94.3 | 111.4 | 145.7 | 162.9 | 180.0 |
| 30 | 8.6 | 17.1 | 25.7 | 42.9 | 60.0 | 77.1 | 94.3 | 111.4 | 145.7 | 162.9 | 180.0 |
| 32 | 8.6 | 17.1 | 25.7 | 42.9 | 60.0 | 77.1 | 94.3 | 111.4 | 145.7 | 162.9 | 180.0 |
| 34 | 8.6 | 17.1 | 25.7 | 42.9 | 60.0 | 77.1 | 94.3 | 111.4 | 145.7 | 162.9 | 180.0 |
| 36 | 8.6 | 17.1 | 25.7 | 42.9 | 60.0 | 77.1 | 94.3 | 111.4 | 145.7 | 162.9 | 180.0 |
| 38 | 8.6 | 17.1 | 25.7 | 42.9 | 60.0 | 77.1 | 94.3 | 111.4 | 145.7 | 162.9 | 180.0 |
| 40 | 8.6 | 17.1 | 25.7 | 42.9 | 60.0 | 77.1 | 94.3 | 111.4 | 145.7 | 162.9 | 180.0 |
| 42 | 8.6 | 17.1 | 25.7 | 42.9 | 60.0 | 77.1 | 94.3 | 111.4 | 145.7 | 162.9 | 180.0 |
| 44 | 8.6 | 17.1 | 25.7 | 42.9 | 60.0 | 77.1 | 94.3 | 111.4 | 145.7 | 162.9 | 180.0 |
| 46 | 8.6 | 17.1 | 25.7 | 42.9 | 60.0 | 77.1 | 94.3 | 111.4 | 145.7 | 162.9 | 180.0 |
| 48 | 8.6 | 17.1 | 25.7 | 42.9 | 60.0 | 77.1 | 94.3 | 111.4 | 145.7 | 162.9 | 180.0 |
| max | 8.6 | 17.1 | 25.7 | 42.9 | 60.0 | 77.1 | 94.3 | 111.4 | 145.7 | 162.9 | 180.0 |

30

METHOD AND COMPUTER UNIT FOR SETTING A CONTRAST AGENT INJECTION PUMP FOR IMAGE RECORDING

PRIORITY STATEMENT

The present application hereby claims priority under 35 U.S.C. §119 on German patent application number DE 10 2006 032 991.0 filed Jul. 17, 2006, the entire contents of which is hereby incorporated herein by reference.

FIELD

Embodiments of the invention generally relate to a method for setting an injection pump for image recording. Embodiments of the invention also generally relate to a computer unit for creating and outputting a contrast agent protocol in order to set an injection pump for image recording.

BACKGROUND

Information about the interior of the object being examined can be obtained by way of image recordings such as these which, in particular, are slice images of different spatial positions of an object. The image recordings may, for example, be obtained by an X-ray computed-tomography scanner, a magnetic resonance imaging scanner, a photon-emission computer-tomography scanner, a positron-emission scanner, or an ultrasound appliance. By way of example, the image recordings can be used to obtain valuable information about the position, the size and the structure of internal organs, of bone tissue or of other soft tissue parts in a patient. In particular, the sequential slice images can also be converted to a three-dimensional display.

The contrast in the images produced of the object, for example of a patient, is created by locally different excitation, absorption, reflection or emission characteristics of the materials being examined with respect to the radiation, particle bombardment or sound waves used by the imaging appliance. In the case of an X-ray appliance, the different absorption or attenuation characteristics of different types of tissue are used to provide contrast. Since, for example, the characteristics of bone tissue and soft tissue parts differ widely, it is possible to analyze the structure of a bone inside the body of a patient on the basis of the contrast associated with this in the images.

Organs or vessels whose characteristics do not differ significantly in order to form contrast with the surrounding tissue in the recorded images cannot be examined in the conventional manner, because the resulting contrast is too low. For this reason, when examining an organ through which blood is flowing, for example a heart, a liver or a vessel in the area of the patient's extremities, a contrast agent is added to the blood circulation of the patient before the start of image recording. The contrast agent results in the organs being examined being imaged with sufficiently great contrast in comparison to the surrounding tissue.

A contrast agent protocol is created for this purpose, and is used to set an injection pump with the contrast agent. By way of example, the contrast agent protocol includes the nature, the volume, the concentration and the flow rate of the contrast agent. In particular, a contrast agent protocol may include a plurality of different feed phases, which differ in the parameters. In complex contrast agent protocols, phases in which, for example, a saline solution is supplied can also be provided between phases in which contrast agent is being fed, can also be provided.

The contrast agent protocol is used to produce a predictable contrast agent profile in the patient, so that the respectively required contrast agent concentration for contrast formation is produced in the examination area while the successive slice images are being recorded.

In general, the contrast agent protocol is not optimized for the individual patient in the clinical routine, since the procedures are kept simple. The patient therefore receives a suboptimum amount of contrast agent, which leads either to an undesirable excess amount, or to an adverse effect in the image quality. Furthermore, the contrast agent protocol is not always matched to a scan protocol for the imaging appliance, which leads to the contrast agent that has been supplied not being in the examination region at the time of image recording, but being there too early or too late.

Some of the parameters which are required to calculate an individual contrast agent protocol, such as the required amount of contrast agent, can be determined accurately only with the aid of image recordings. The contrast agent is therefore drawn into the injection pump only during the examination, thus making the procedure worse, and lengthening the examination time.

SUMMARY

In at least one embodiment, the invention allows an injection pump to be set easily and quickly.

According to at least one embodiment of the invention, a method is for setting an injection pump for image recording, in which patient-specific and appliance-specific input parameters are entered, a contrast agent protocol is created from the patient-specific and appliance-specific input parameters, by computer, by way of a functional relationship, and is output for or to the injection pump.

At least one embodiment of the invention is based on the idea that the procedure for setting an injection pump is particularly simple and quick if a contrast agent protocol is created and output automatically to the injection pump. For this purpose, first of all, patient-specific and appliance-specific input parameters are entered in a computer unit in order to create the contrast agent protocol, or are read in from the computer unit if the parameters have already been stored, and can be accessed, for example in the form of a patient file. By way of example, the patient's weight, the patient's size and the organ to be examined as well as the distance between the organ or the region being examined and the point at which the contrast agent is supplied can be taken into account as patient-specific input parameters, which can be defined with the necessary accuracy and do not change over the course of the image recording and the examination of the patient. In addition, the heart minute volume (HMV) or the heart time volume (HTV) can be used as patient-specific input parameters for creation of the contrast agent protocol, that is to say the volume of the blood which is pumped through the blood circulation by the heart in one minute, if this volume can be defined accurately.

By way of example, one appliance-specific input parameter is the scan duration, which must be correlated with the rate of propagation of the contrast agent in the blood circulation of the patient, and is set in an imaging appliance that is used to make the image recordings.

The contrast agent protocol is then created by way of a stored functional relationship which, in particular, is implemented in a software program or is stored in a data memory, on the basis of the entered input parameters. In this case, the functional relationship may include empirical associations, simple rules of thumb, mathematical formulae or else complex computation models which are based on fuzzy logic or on a neural network.

The final method step includes the contrast agent protocol which has been created being output for or to the injection pump. The contrast agent protocol can then either be transferred manually to the injection pump, or this is done by a data transfer via a suitable link, in order to set the injection pump automatically.

Because of the high degree of automation of the method, the creation of a customized contrast agent protocol for image recording involves very little time and effort for the operator of the imaging appliance. Furthermore, the method is distinguished by good reproducibility, contrast image quality, as well as by particularly good utilization and patient-protective metering of the contrast agent.

One particularly simple embodiment of the functional relationship, which requires very little computational effort and memory, is advantageously to use an association, which is contained in particular in a table, of the input parameters with the output parameters of the contrast agent protocol as the functional relationship. In this case, the expression output parameters means all of the variables contained in the contrast agent protocol, such as the amount or volume of the contrast agent, the flow rate, the contrast agent concentration, etc. By way of example, the table represents a compilation of empirical data, with a separate table being provided for each output parameter from the contrast agent protocol. The empirical numerical values of the output parameter are entered in this table as a function of two input parameters, for example the patient weight and the scan duration.

In particular, a set including a plurality of tables is provided, with a dedicated table being assigned to each output parameter. Alternatively, the cells in a single table may have a more complex structure. The numerical values for a plurality of input parameters are entered in the header and in the left-hand column of this table which, in particular, is also multidimensional, and the individual table cells contain various contrast agent protocols, for example based on a list with the output parameters.

Alternatively or in conjunction with an association contained in a table, mathematical and/or logical operations are preferably used as part of fuzzy logic in the functional relationship. The advantage of this embodiment is that the fuzzy logic can be used even if no exact correlation is known between the input and output parameters. The fuzzy logic has a self-learning capability and is able to set up mathematical formulations which are successfully implemented in a computer system for automated creation of the contrast agent protocol.

According to one preferred variant of at least one embodiment, the functional relationship is changed on the basis of empirical values. The method is therefore distinguished by very high flexibility since the user of the software program is provided with the capability to edit the functional relationship, and to match it to his own experience. The expression empirical values refers to, for example, the experiences of the user from previous examinations or the experiences of the software program based on automated image processing or based on semi-automatic image processing, for which the user enters specific image quality features. In the case of automatic or semi-automatic methods for image processing, the functional relationship can be changed by the software program, without any user interaction.

According to a further preferred variant of at least one embodiment, an estimated scan duration is specified as an appliance-specific input parameter. The scan duration is normally unknown at the start of the examination, since it must be matched to the propagation of the contrast agent in the patient's body. The propagation of the contrast agent is a highly dynamic process, which is highly dependent on the physical constitution of the patient. In these circumstances, an empirical numerical value for the scan duration is entered at the start of the examination, and is first of all used to determine values for the output parameters which are close to the actual values. A provisional contrast agent protocol is therefore created.

Before the start of the examination, a provisional amount of contrast agent is expediently determined from the estimated scan duration as part of the contrast agent protocol. In contrast to the known procedure, in which the amount of contrast agent is determined only during the course of the examination, thus lengthening the examination duration, an amount of contrast agent is in this case available even at the start of the examination. The contrast agent protocol and the amount of contrast agent need be adapted only in a situation in which it is found during the course of image recording that the actually required amount of contrast agent differs significantly from that determined.

Once the contrast agent protocol has been created and the provisional amount of contrast agent defined, this provisional amount of contrast agent is drawn, preferably automatically, by the injection pump, and is provided for image recording. The amount of effort by the operator of the imaging appliance is therefore reduced to a minimum, and the examination can be started without delay, as soon as the patient has been positioned on a patient couch.

One example refinement of at least one embodiment provides a matched couch feed rate for the patient couch, and/or a matched rotation rate of the imaging appliance being output with the contrast agent protocol in order to comply with the estimated scan duration. Adaptation of the couch feed rate and/or the rotation rate not only achieves compliance with the scan duration but also ensures that the entire amount of contrast agent determined for this scan duration is used. In this case, no analysis is required in order to determine a more accurate scan duration or amount of contrast agent. This refinement is particularly simple, and can be used easily. It is also possible to provide for a scan delay time to be output with the contrast agent protocol. The scan delay time represents the time interval between the supply of the contrast agent and the scan start. A contrast level for the measurement start can also be output for a bolus tracking method, and the intermediate scan delay, with the contrast agent protocol. These parameters can also be adapted on a patient-specific basis.

According to one alternative example refinement of at least one embodiment, an actual scan duration is determined, and is entered as a corrected input parameter, during image recording. This makes it possible to use a conventional proven method for determining the rate at which the contrast agent propagates in the blood circulation of the patient, and therefore the required scan duration, for example during the course of a computed-tomography scan for definition of the size of the area to be examined, taking account of the scanning rate of the imaging appliance. The contrast agent protocol can be adapted by inputting the actual scan duration. This refinement is therefore distinguished by its accuracy.

An actual amount of contrast agent is advantageously determined on the basis of the actual scan duration, as part of the contrast agent protocol. The actual amount of contrast agent can be used in particular as an orientation value, in order to find out whether more contrast agent should be added to the injection pump or whether less contrast agent is being consumed than originally intended.

Adaptations to the contrast agent protocol and/or to the procedure are carried out in particular automatically by the software program. For this purpose, the amount of contrast agent drawn is compared with the actual amount of contrast agent, and in the situation where the actual amount of contrast agent is greater than the provisional amount of contrast agent, an addition of a dilution agent or the request for replenishment of the injection pump is output as part of the contrast agent protocol. The addition of a dilution agent, for example of a saline solution, is worthwhile in particular if there is a small difference between the amount drawn and the amount actually required. If the difference between the two amounts is large, it is advantageous, with regard to the image recording quality, for additional contrast agent to be drawn and used.

If the comparison of the two amounts of contrast agent shows that the actual amount of contrast agent is less than the provisional amount of contrast agent (which has been drawn in the injection pump in advance), a shorter injection time is preferably output as part of the contrast agent protocol. The supply of contrast agent is stopped when the amount supplied has reached the actual amount. The major advantage in this case is that the desired image quality is achieved, and the patient is not loaded with an excessive amount of contrast agent.

The decision as to whether a changed contrast agent protocol is output preferably depends on a threshold value. The threshold value may be both a stored organ-specific value and a user-defined value, which is specified at the start of each new examination. In particular, the threshold value can be changed at any time. If it is found during the comparison of the amount of contrast agent drawn with the actual amount of contrast agent that the difference found between the two amounts is greater than the threshold value, then the steps as described above are initiated in order to update the contrast agent protocol. However, if the threshold value has not been exceeded, there is no need to adapt the contrast agent protocol. This means that, in a situation in which the amount of contrast agent drawn is greater than the amount required and is within the tolerance range defined by the threshold value, the entire amount drawn is supplied, thus increasing the confidence that the examination scan will be carried out precisely when the contrast agent is in the examination region.

Threshold values can also be used to keep the amount of contrast agent within specific limits, within which the amount supplied will not be injurious to the health of the patient, as a function, for example, of the age or the weight of the patient.

A highly customized method is provided by expediently calculating the threshold value as a function of the patient-specific input parameters.

In at least one embodiment, a computer unit is designed to create and output a contrast agent protocol in order to set an injection pump for image recording.

The advantages and preferred refinements relating to at least one embodiment of the method can be transferred in the same sense to the computer unit.

BRIEF DESCRIPTION OF THE DRAWINGS

Embodiments of the invention will be explained in more detail in the following text with reference to the drawings, in which:

FIG. 2 shows a table showing how a volume of contrast agent is determined during a phase in which contrast agent is being supplied.

DETAILED DESCRIPTION OF THE EXAMPLE EMBODIMENTS

Figure 1:
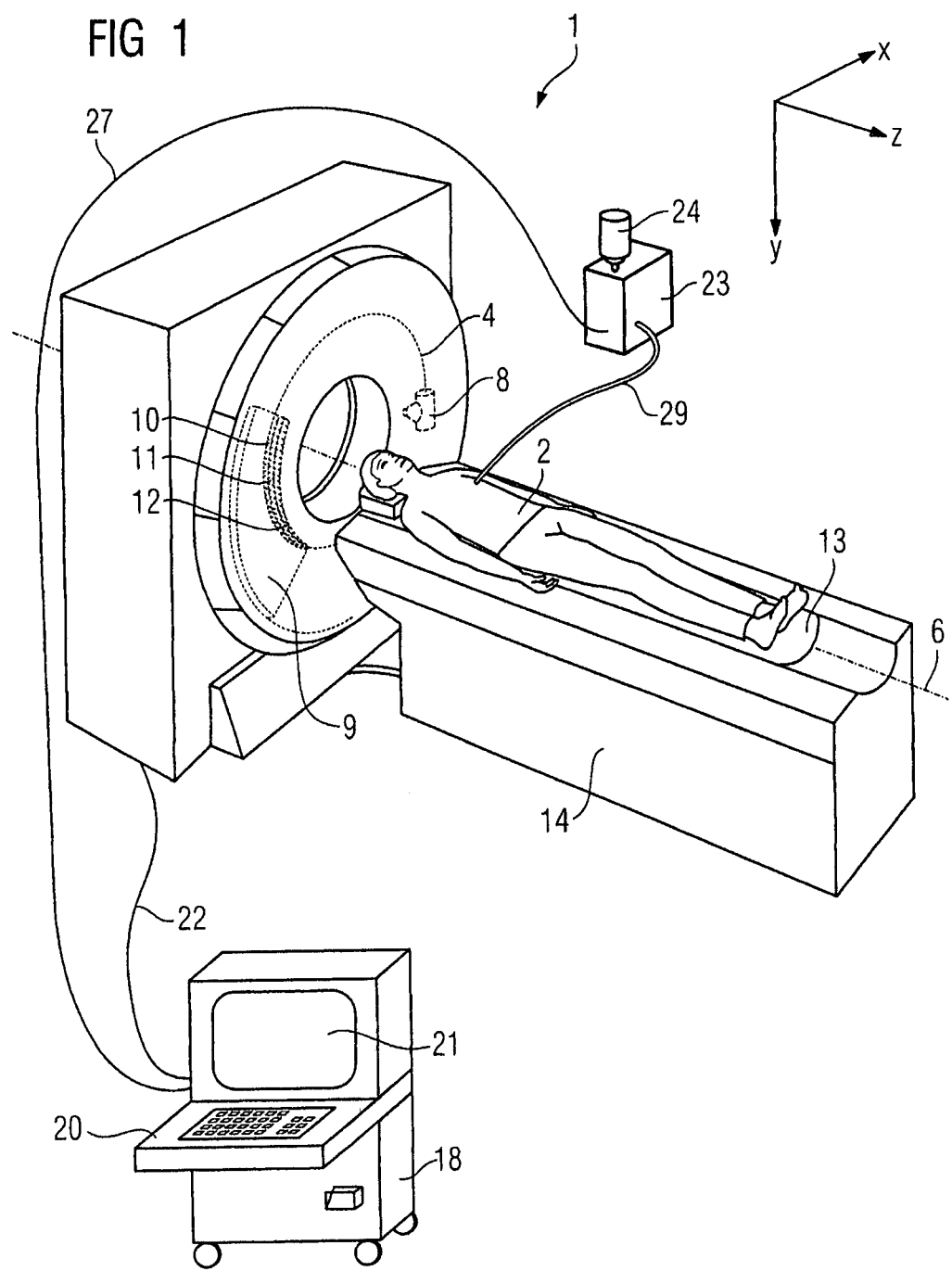
FIG. 1 shows a perspective illustration of an X-ray computed-tomography scanner as an imaging appliance.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows a computed-tomography scanner 1 as an imaging appliance for examination of an object, in this case a patient 2. The computed-tomography scanner 1 has a radiation source 8, which is arranged in a gantry 4 such that it can rotate about a rotation axis 6, for transmission of X-ray radiation. A curved detector 9 is arranged opposite the radiation source 8, comprising a plurality of detector elements arranged to form detector rows 10, 11, 12.

The computed-tomography scanner 1 also has a patient couch 13, which is mounted such that it can be moved along the rotation axis 6 on a table 14.

A computing unit is shown as a further component of the computed-tomography scanner 1 and is also referred to as a control unit 18, which has a control console 20 and a graphics display unit 21. The control unit 18 is connected to the computed-tomography scanner 1 via a control line 22.

The control unit 18 is designed to drive the feed for the moving patient couch 13 and the rotation of the gantry 4 in order to record sequential slice images. The gantry 4 and the patient couch 13 together form a positioning unit which makes it possible to record slice images at different spatial positions of the patient 2. A scanning rate for the computed-tomography scanner 1 can be set by way of the ratio of the rotation rate of the gantry 4 and the feed rate of the patient couch 13. In this case, the rotation of the gantry 4 ensures that a slice image is recorded at one longitudinal position of the patient 2, while in contrast, the feed of the patient couch 13 is responsible for the sequence of slice images to be recorded.

The X-ray radiation transmitted from the radiation source 8 and passing through the patient 2 is detected by the detector 9 in order to record a slice image. In the case of the illustrated computed-tomography scanner 1, the radiation source 8 produces a fan-shaped X-ray beam for this purpose. A characteristic attenuation image of the X-ray radiation is therefore recorded in each position of the gantry 4. A slice image is reconstructed from the projections obtained in the various positions of the gantry 4, on which slice image tissue with different attenuation characteristics is represented by different grey-scale values.

A contrast agent is added in order to examine organs through which blood is passing, for example a heart, a liver or a blood vessel. For this purpose, the control unit 18 is connected via a control line 27 to an injection pump 23, via which a contrast agent 24 is supplied in a controlled manner to the patient 2 by way of a flexible contrast agent tube 29, in accordance with the predetermined contrast agent protocol. As parameters for the supply of contrast agent, the respective contrast agent protocol includes, in particular, a number of different supply phases, which each differ in the nature of the agent being supplied, its concentration, its flow rate and the absolute amount.

A software program is provided in order to control the computed-tomography scanner 1 as well as the injection pump 23 before and during the examination of the patient, and a functional relationship between the patient-specific and appliance-specific input parameters and output parameters of the contrast agent protocol is implemented in this software program. The functional relationship includes, in particular, empirical data and associations, which are combined in a table (see FIG. 2). Logical conclusions are in this case drawn by means of the fuzzy logic in order to determine the contrast agent protocol. The functional relationship is independently adapted on the basis of the input parameters which have been entered or determined during the course of the examination, for the contrast agent protocol.

Before the examination, the patient 2 is registered and his or her patient-specific input parameters are entered manually in the software program or are read from a database by the software program if, for example, a patient file with the required information has already been produced. The patient-specific input parameters, which are known and can be extended, are, for example, the type of examination (for example the organ to be examined, in this exemplary embodiment the heart), the patient's weight, the patient's size, the patient's age, the blood pressure and possibly further blood parameters.

These parameters are used by the fuzzy logic in the software program in order to output a suitable scan duration. In this case, the scan duration is defined on the basis of the following fundamental relationships:

large patient→large organ→large scan area→long scan duration small patient→small organ→small scan areas→short scan duration A provisional contrast agent protocol is produced just using the input parameters in the estimated scan duration. The contrast agent protocol is collated from a plurality of output parameters and, for example, uses a table 30 for each output parameter, as is shown in FIG. 2. The contrast agent protocol includes a plurality of supply phases, which differ in the nature, the volume and the flow rate of the agent being supplied. The contrast agent protocol appears, for example, as follows:

Phase 1 (supply of contrast agent)
Contrast agent type
Volume: 60 ml
Flow rate: 4 ml/s
  Phase 2 (supply of contrast agent)
Contrast agent type
Volume: 20 ml
Flow rate: 3 ml/s
  Phase 3 (supply of saline solution)
Saline solution
Volume: 150 ml
Flow rate: 3 ml/s
  Proposal for determining the scan delay time:
  bolus tracking
  contrast level for measurement start: 100 HU (Hounsfield Units)
  examination region (Region of Interest, ROI): rising aorta
Intermediate scan delay: 5 s In this example embodiment, the software program adapts the contrast level for the measurement start, as well as the intermediate delay. Analogously to the determination of the optimized injection parameters, the adaptation is in this case based on the patient-specific input parameters and the determined examination parameters.

The total required volume is calculated and output by addition of the amounts of contrast agent 24 and saline solution required for the individual phases. The operator must connect containers with an adequate content to the injection pump 23 in an appropriate manner, and the calculated provisional amount is then drawn automatically by the injection pump 23. By way of example, for the contrast agent protocol described above, 80 ml of contrast agent 24 is drawn into a first syringe, and 150 ml of saline solution into a second syringe.

After determining the provisional contrast agent and saline solution amounts, the examination of the patient, who is positioned on the patient couch 13 and is connected to the injection pump 23, can be started. Firstly, a topogram scan is carried out, and is used to define the area to be scanned. Once the size of the area to be scanned has been determined in this way, the exact or actual scan duration can be determined taking into account the known feed rate of the patient couch 13 and the rotation rate of the gantry 4.

First of all, an analysis is carried out to determine the so-called "Contrast Mean Transit Time" (CMT), that is to say the time which the injected contrast agent 24 requires to reach the area to be scanned. An analysis such as this can be carried out, for example, using a test bolus. In this case, the exact time data for the examination is also available. The input parameters can be adapted and an optimized monitoring agent protocol can be output on the basis of the variables measured and determined in this way.

A check is then carried out to determine whether the newly output parameters and, possibly, the CMT are within a standard range. For example, a check is carried out to determine whether the provisional amount that has been drawn is sufficient for the optimum protocol. The criteria for this decision are in the form of threshold values, depend on the chosen examination, and can be configured by the user.

Example 1: for a heart examination, 5% less contrast agent 24 is determined and drawn than the actual (optimum) amount of contrast agent. A 5% discrepancy is within the selected tolerance limits. In this case, the contrast agent 24 is diluted somewhat with saline solution in the second phase, and the contrast agent protocol is retained. However, if the difference between the amount of contrast agent drawn and that actually consumed is outside the tolerance range, then a signal is output to the operator, for example: "draw 20 ml more contrast agent".

Example 2: more contrast agent 24 was drawn than was actually consumed. If the difference between the amount drawn and the amount actually used is within the selected tolerance range, the contrast agent protocol is retained, and the entire amount of contrast agent drawn is supplied. If the difference is outside the tolerance band, then contrast agent 24 is left over.

A safety check can optionally also be carried out in order to check whether the amount of contrast agent is within a range that is safe for the patient. In this case, the patient can be examined for contrast agent allergies, kidney insufficiency, thyroid hormones, etc., and his or her age can be taken into account.

According to an alternative procedure, the estimated scan duration is assumed as a constant, and is stored. After definition of the area to be scanned, by means of the tomogram scan, the couch feed rate of the patient couch 13 and the rotation rate of the gantry 4 are adapted such that the scan duration can be complied with. The other method steps remain the same, except for the output of an optimized contrast agent protocol, which is not required for this alternative method.

An example of a table 30, with which the provisional amount of contrast agent (in particular volume) is determined for a first supply phase as a function of the patient's weight and the estimated scan duration, is shown in FIG. 2. The weight of the patient 2 is shown in kilograms in the header. The left-hand column contains the estimated scan duration in seconds. The table contents are based on empirical values, and can be changed by the user.

One table such as that shown in FIG. 2 is provided for each output parameter. A table set comprising a plurality of tables is therefore produced overall, which contain empirical values and can be changed by the user of the software program on the basis of his or her own experience.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for setting an injection pump for image recording, comprising:
    entering patient-specific and appliance-specific input parameters, an estimated scan duration being entered as an appliance-specific input parameter;
    creating a contrast agent protocol from the entered patient-specific and appliance-specific input parameters, by computer, by way of a functional relationship, a provisional amount of contrast agent being determined from the estimated scan duration as part of the contrast agent protocol before the start of image recording;
    outputting, to the injection pump, the contrast agent protocol, the provisional amount of contrast agent being drawn automatically by the injection pump;
    determining an actual scan duration;
    entering, during image recording, the actual scan duration as an appliance-specific input parameter;
    determining an actual amount of contrast agent as part of the contrast agent protocol based on the actual scan duration;
    comparing the provisional amount of contrast agent to the actual amount of contrast agent; and
    outputting, if the actual amount of contrast agent is greater than the provisional amount of contrast agent, at least one of a request to add a dilution agent and a request for replenishment of the injection pump as part of the contrast agent protocol.

2. The method of claim 1, wherein at least one of mathematical and logical operations are used as part of fuzzy logic in the functional relationship.

3. The method as claimed is claim 1, further comprising:
    chancing the functional relationship on the basis of empirical values.

4. The method as claimed in claim 1, further comprising:
    outputting at least one of a matched couch feed rate for a patient couch and a matched rotation rate of an imaging appliance with the contrast agent protocol in order to comply with the estimated scan duration.

5. The method as claimed in claim 1, further comprising: outputting, if the actual amount of contrast agent is less than the provisional amount of contrast agent, a shorter injection time is output as a part of the contrast agent protocol.

6. A non-transitory computer readable medium comprising program segments for, when executed on a computer device, causing the computer device to implement the method of claim 1.

7. The method in claim 1, wherein an association of the entered patient-specific and appliance-specific input parameters with output parameters of the contrast agent protocol is used as the functional relationship.

8. The method as claimed in claim 7, wherein the association of the entered patient-specific and appliance-specific input parameters with the output parameters of the contrast agent protocol is contained in a table.

9. The method as claimed in claim 7, wherein at least one of mathematical and logical operations are used as part of the fuzzy logic in the functional relationship.

10. The method as claimed in claim 1, further comprising: outputting a changed contrast agent protocol as a function of a threshold value.

11. The method in claim 10, wherein the threshold value is calculated as a function of the patient-specific input parameters.

12. A computer unit, designed to create and output a contrast agent protocol, to set an injection pump for image recording, comprising:
the computer unit configured to,
receive entered patient-specific and appliance-specific input parameters, an estimated scan duration being entered as an appliance-specific input parameter;
create a contrast agent protocol from the entered patient-specific and appliance-specific input parameters, by computer, by way of a functional relationship, the computer unit determining a provisional amount of contrast agent from the estimated scan duration as part of the contrast agent protocol before the start of image recording;
output to the injection pump, the contrast agent protocol, the provisional amount of contrast agent being drawn automatically by the injection pump;
determine an actual scan duration:
enter, during image recording, the actual scan duration as an appliance-specific input parameter;
determine an actual amount of contrast agent as part of the contrast agent protocol based on the actual scan duration;
compare the provisional amount of contrast agent to the actual amount of contrast agent; and
output, if the actual amount of contrast agent is greater than the provisional amount of contrast agent, at least one of the request to add a dilution agent and a request for replenishment of injection pump as a part of the contrast agent protocol.

13. The computer unit as claimed in claim 12, wherein the computer unit is configured to output, if the actual amount of contrast agent is less than the provisional amount of contrast agent, a shorter injection time is output as part of the contrast agent protocol.

14. A computer unit, to create and output a contrast agent protocol, to set an injection pump for image recording, comprising:
means for receiving entered patient-specific and appliance-specific input parameters, an estimated scan duration being entered as an appliance-specific input parameter;
means for creating a contrast agent protocol from the entered patient-specific and appliance-specific input parameters by way of a functional relationship, a provisional amount of contrast agent being determined from the estimated scan duration as part of the contrast agent protocol before the start of image recording;
means for outputting, to the injection pump, the contrast agent protocol, the provisional amount of contrast agent being drawn automatically by the injection pump;
means for determining an actual scan duration;
means for entering, during image recording, the actual scan duration as an appliance-specific input parameter;
means for determining an actual amount of contrast agent as part of the contrast agent protocol based on the actual scan duration;
means for comparing the provisional amount of contrast agent to the actual amount of contrast agent; and
means for outputting, if the actual amount of contrast agent is greater than the provisional amount of contrast agent, at least one of a request to add a dilution agent and a request for replenishment of the injection pump as part of the contrast agent protocol.

* * * * *